(12) United States Patent
Blatt et al.

(10) Patent No.: US 11,833,070 B1
(45) Date of Patent: Dec. 5, 2023

(54) SIDES-DOWN, OPEN DOOR PRESSURE RELIEF BOOT

(71) Applicant: N.Y. Orthopedic USA, Inc., Brooklyn, NY (US)

(72) Inventors: Michael J. Blatt, Brooklyn, NY (US); Michael A. Rozenberg, Monsey, NY (US)

(73) Assignee: N.Y. Orthopedic USA, Inc., Brooklyn, NY (US)

( * ) Notice: Subject to any disclaimer, the term of this patent is extended or adjusted under 35 U.S.C. 154(b) by 0 days.

(21) Appl. No.: 17/949,355

(22) Filed: Sep. 21, 2022

Related U.S. Application Data

(60) Provisional application No. 63/353,209, filed on Jun. 17, 2022.

(51) Int. Cl.
*A61F 5/00* (2006.01)
*A61F 5/01* (2006.01)
*A61F 13/06* (2006.01)

(52) U.S. Cl.
CPC .......... *A61F 5/0195* (2013.01); *A61F 5/0111* (2013.01); *A61F 13/06* (2013.01)

(58) Field of Classification Search
None
See application file for complete search history.

(56) References Cited

U.S. PATENT DOCUMENTS

| | | | | |
|---|---|---|---|---|
| 5,328,445 A | * | 7/1994 | Spahn | A61F 5/05816 128/882 |
| 8,858,478 B2 | * | 10/2014 | Purdy | A61H 9/005 128/DIG. 20 |
| 2012/0253250 A1 | * | 10/2012 | Spahn | A61F 5/0127 602/13 |
| 2016/0256329 A1 | * | 9/2016 | Spahn | A61F 13/064 |

FOREIGN PATENT DOCUMENTS

WO WO-2009042045 A1 * 4/2009 ............ A61F 5/0111

OTHER PUBLICATIONS

Medictests, LLC, "Standard Anatomical Terms and Planes," https://medictests.com/units/standard-anatomical-terms-and-planes, Retrieved on Jan. 3, 2021.
"Anatomy of a Boot-Axe and Boots," http://www.axeandboots.com/blog/structure/anatomy-of-a-boot/, Feb. 28, 2017.
ScienceAid.net, "The Bones of the Human Leg and Foot," https://scienceaid.net/Bones_of_the_Human_Leg_and_Foot, Retrieved on Jul. 6, 2022.

(Continued)

*Primary Examiner* — Kim M Lewis

(74) *Attorney, Agent, or Firm* — Bochner PLLC; Andrew D. Bochner

(57) ABSTRACT

Apparatus and methods for a therapeutic boot that promotes the healing of pressures sores is described. Bedridden patients are prone to developing pressure sores over bony prominences of the foot such as a heel. The therapeutic boot includes a sides-down, open door design that provides unobstructed access to a wound site. The therapeutic boot (Continued)

may be designed to offload the patient's heel and bony prominences on both sides of the patient's ankle. The therapeutic boot is designed such that opening and closing the boot does not apply pressure and or friction to the wound site.

20 Claims, 8 Drawing Sheets

(56) References Cited

OTHER PUBLICATIONS

The Cleveland Clinic Foundation, "Foot and Toe Ulcers," https://my.clevelandclinic.org/health/diseases/17169-foot-and-toe-ulcers, Retrieved on Jul. 20, 2022.

The Johns Hopkins University, "Foot Ulcers," https://www.hopkinsmedicine.org/health/conditions-and-diseases/diabetes/foot-ulcers, Retrieved on Jul. 20, 2022.

The University of Michigan Health System, "Frequently Asked Questions: Diabetic Foot Ulcers," https://www.uofmhealth.org/conditions-treatments/podiatry-foot-care/frequently-asked-questions-diabetic-foot-ulcers, Retrieved on Jul. 20, 2022.

Alpolink (UK) Limited, "Parts of the Human Body," https://www.easypacelearning.com/all-lessons/English-level-2/774-parts-of-the-human-body-parts-learning-english-body-parts-words, Retrieved on Jul. 6, 2022.

thewirecutter.com, "The Best Hiking Boots," https://www.pintrest.com/pin/the-best-hiking-boots--465207836501341158/, Retrieved on Jul. 6, 2022.

Truman Boot Co., "Anatomy of a Boot," https://www.trumanboot.com/pages/anatomy-of-a-boot, Retrieved on Jul. 6, 2022.

EHOB Inc., "TruVue Heel Protector," www.ehob.com/products/truvue-heel-protector/, Retrieved on Jul. 21, 2022.

\* cited by examiner

SIDES-DOWN, OPEN DOOR PRESSURE RELIEF BOOT

CROSS-REFERENCE TO RELATED APPLICATION

This application is a non-provisional of U.S. Provisional Patent Application No. 63/353,209 titled "SIDES-DOWN, OPEN DOOR PRESSURE RELIEF BOOT" filed on Jun. 17, 2022, which is hereby incorporated by reference herein in its entirety.

FIELD OF TECHNOLOGY

This application describes a therapeutic boot that supports a patient's lower extremity while alleviating pressure and friction on or near an injury site, such as a pressure sore, on the lower extremity.

BACKGROUND

Bedridden patients may develop pressure sores. Such pressure sores develop because of prolonging pressure which causes breakdown of skin and other tissue. Because the bedridden patient is immobile, it is difficult to relieve pressure that causes the skin and tissue breakdown. Therefore, pressure sores typically do not heal quickly and have a high recurrence rate. Symptoms of pressure sores may include swelling, burning, and pain. Pressure sores are very sensitive and even the slightest contact with the injury area may cause pain to the patient.

Bodily "contact points" are particularly vulnerable to developing pressure sores. Bodily contact points may refer to areas where prolonged pressure is concentrated on a smaller surface area instead of the pressure being spread out over a relatively larger surface area. For example, bedridden patients have a high risk of developing pressures sores on or near their lower extremities such as a foot, ankle, or heel. The foot, ankle and heel are each associated with bony protrusions that bear the brunt of prolonged pressure and are therefore more prone to developing pressures sores.

It is important to aggressively address pressures sores. If a pressure sore is left untreated, it may increase in size/depth, become infected and, in some cases, require amputation. For example, 24% of people with diabetes that develop a pressure sore on their foot eventually need an amputation. Conventional treatments for pressure sores on a lower extremity such as a foot may include regular wound care and off-loading the injury site. Pressure sores may also be treated using surgical techniques, such as surgical debridement. However, any treatment of a pressure sore typically requires relieving pressure ("offloading") at or near the injury site for a period of time. For example, after a surgical procedure, a typical off-loading period may be as long as four months.

However, it has been challenging to develop a device that effectively offloads an injury site, adequately protects the injury site from further irritation and allows unobstructed access to the injury site for ongoing wound care.

For example, the TruVue® Heel Protector (available from EHOB, Inc. of Indianapolis, Indiana) includes a gate that provides access to a plantar surface of a patient's foot. However, the gate cannot be easily opened for a practitioner to visually inspect an injury site. Opening the gate requires separating a two interleaving flaps from each other. Simply separating the outer flap alone does not provide visual access to the plantar surface.

To obtain visual access to the plantar surface, the outer flap must be sufficiently separated such that the inner flap can also be pulled away from the plantar surface. Even after completely separating the two flaps, the practitioner must hold the flaps apart from each other to maintain an unobstructed view of the injury site. Furthermore, because the inner flap is positioned close to, if not touching, the plantar surface, separating the two flaps from each other may apply unintended pressure to the plantar surface, painfully irritating the injury site.

Accordingly, it would be desirable to provide an improved device that effectively offloads a pressure sore injury and allows access to the injury site without painfully irritating the injury site. Additionally, it would be desirable to provide an improved device that provides unobstructed visual access to the injury site without applying unintended pressure to a pressure sore injury. Therefore, it is desirable to provide apparatus and methods for a SIDES-DOWN, OPEN DOOR PRESSURE RELIEF BOOT.

BRIEF DESCRIPTION OF THE DRAWINGS

The objects and advantages of the disclosure will be apparent upon consideration of the following detailed description, taken in conjunction with the accompanying drawings, in which like reference characters refer to like parts throughout, and in which.

DETAILED DESCRIPTION

Figure 1:
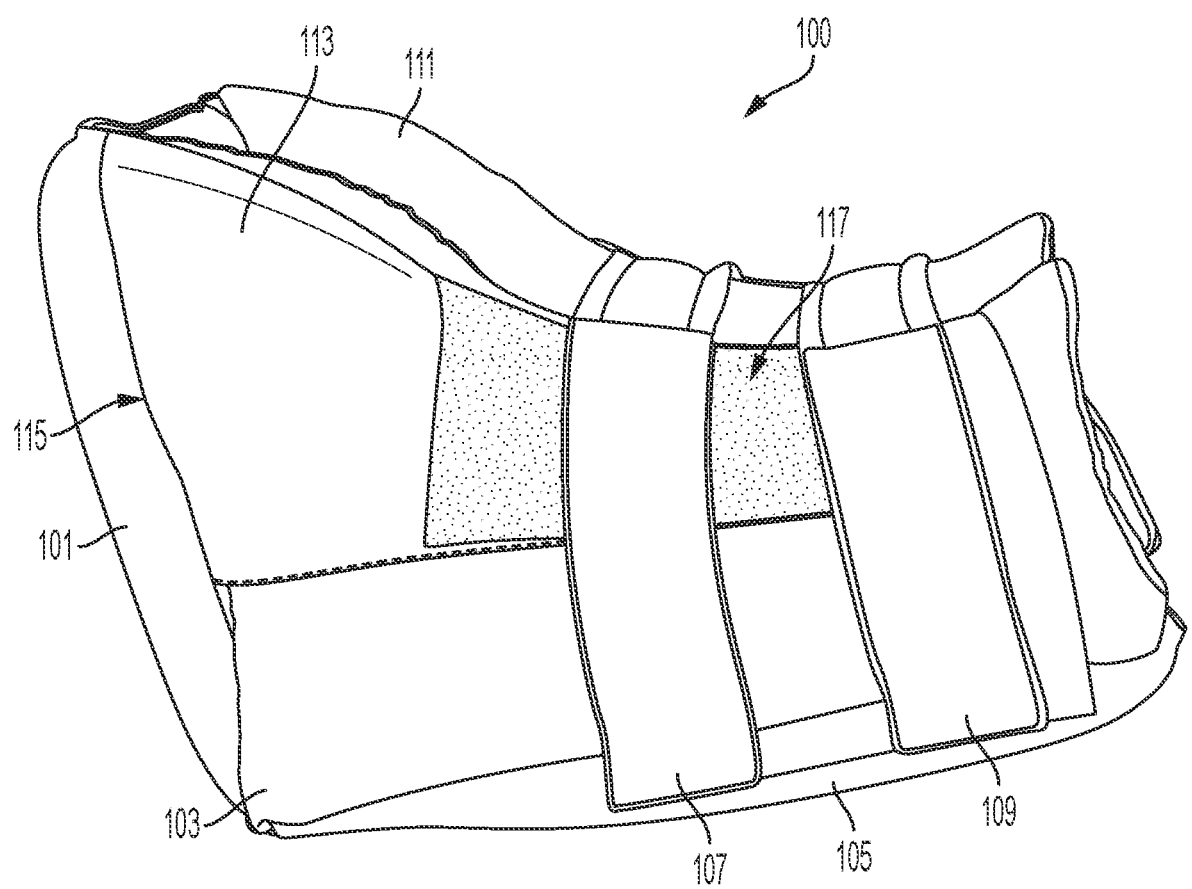
FIG. 1 shows an illustrative boot in accordance with principles of the disclosure.

A therapeutic boot configured to offload a heel of a patient's foot is provided. The boot may offload, or relive pressure from, the heel to prevent a pressure sore from developing on the heel. The boot may offload the heel to promote healing of a pressure sore on or near the heel. The boot may include an upper. The upper may cover the sides and back of the patient's foot.

The upper may include a fabric inner layer and a nylon outer shell. The nylon outer shell may include an antimicrobial coating. The upper may include a microfiber filling. The microfiber filling may provide a thickness, such that when a segment of the upper is positioned underneath the patient's leg, the patient's foot is suspended above a surface supporting the patient.

The upper may include a first segment, a second segment and a third segment. The first segment of the upper may be configured to cover a medial side of the human leg. The medial side may refer to a part of the human body located relatively closer to a midline of the patient's torso.

A second segment of the upper may be configured to cover a dorsal side of the human leg. The dorsal side may refer to a back of the patient. Generally, a bedridden patient may be supported by a surface (e.g., mattress) positioned underneath a back of the patient.

The second segment of the upper may elevate the human leg. The second segment of the upper may elevate the human leg above the surface supporting the patient. The second segment of the upper may define a cut-out. The cut-out may relieve or prevent application of pressure on a heel of the patient's elevated foot. A third segment of the upper may be configured to cover a lateral side of the human leg. The lateral side may refer to a part of the human body located relatively further away from the midline of the patient's torso.

The first segment of the upper may be rotatable with respect to the second segment. The third segment of the upper may be rotatable with respect to the second segment. The upper may include a strap. The strap may be configured to releasably affix the first segment to the third segment. The boot may be configured to leave a ventral side of the patient's leg or foot uncovered. The ventral side may refer to a front of the patient. The strap may pass over the uncovered ventral side to connect the first segment to the third segment.

The boot may include a sole. The sole may be positioned to cover a plantar surface of a patient's foot. The sole may be affixed to the upper by a hinge. The hinge may allow the sole to rotate between an open position and a closed position. In the closed position, the sole may cover the plantar surface. In the closed position, the sole may protect the plantar surface from contact with bedsheets or other items that may apply unintended pressure to an injury site.

In the open position, the sole may be positioned to allow access to the plantar surface of the patient's foot. In the open position, the sole may be positioned at an angle between 0 and 90 degrees relative to a longitudinal axis of the second segment of the upper that is positioned underneath the dorsal portion of the patient's leg. In the open position, the sole may be positioned at an angle greater than 90 degrees relative to the longitudinal axis of the second segment of the upper.

In the open position, gravity may keep the sole positioned away from the plantar surface of the patient's foot. In the open position, the sole may be separated from the upper in a manner that provides an unobstructed view of the plantar surface and other parts of the patient's foot/leg. The sole may be between the open and closed positions. For example, the sole may be partially pulled apart from the upper and allow a practitioner to view the injury site (e.g., on the patient's toe) without exposing the entire plantar surface The hinge affixing the upper to the sole may be a first hinge. The sole may be rotatably affixed to the upper by the first hinge and a second hinge. The first and second hinges may define an axis of rotation. The sole may rotate about the axis of rotation when transitioning from the closed position to the open position. The sole may rotate about the axis of rotation when transitioning from the open position to the closed position.

The boot may suspend the heel over a space between the first and second hinges. The space between the first and second hinges may be defined by the cut-out defined by the second segment of the upper. Suspending the heel may offload an injury site at or near the heel.

The boot may include a first flap. The first flap may releasably affix a first side of the sole to the upper. The boot may include a second flap. The second flap may releasably affix a second side of the sole to the upper. The sole may be separable from the upper by releasing the first and second flaps from the upper. Releasing the first and second flaps from the upper may not apply pressure to the plantar surface.

A first end of the first flap may be affixed to the sole. The first end of the first flap may be rotatably affixed to the sole. A second end of the first flap may be releasably affixable to the upper. The second end of the first flap may be released from the upper to allow the first side of the sole to be separated from the upper. A first end of the second flap may be rotatably affixed to the sole. A second end of the second flap may be releasably affixable to a second side of the upper. The second end of the second flap may be released to allow the second side of the sole to be separated from the upper.

The second ends of the first or second flap may be releasably affixed to the upper, such that the second ends can be separated from the upper by pulling the second ends away from the patient's foot and/or leg. For example, the second ends of the first and/or second flaps may be releasably affixed to the upper using hook-and-loop fasteners, such as those offered under the Velcro® brand (available from Velcro USA Inc. of Manchester, New Hampshire). In such embodiments, because the first ends of the first or second flap are rotatably affixed to the sole, separating the second end from the upper does not apply any moment of rotation to the sole.

Thus, the second ends of the first or second flaps may be separated from the upper without applying any pressure to the patient's foot and/or leg, thereby minimizing any irritation to a pressure sole injury on the patient's foot and/or leg. After separating the first and/or second flap from the upper, the sole can be rotated into the open position. Because the sole is rotatably affixed to the upper via the hinge, the sole can be moved into the open position without applying any rotational moment or pressure to the upper or the patient's foot and/or leg.

Exposing the patient's foot and/or leg by rotating the sole relative to the upper allows a practitioner to obtain access to a pressure sore injury site without any risk of irritating the injury site. Additionally, the sole can be rotated about the hinge such that the entire plantar surface of the patient's foot is exposed. Thus, the boot design described herein allows a practitioner to obtain an unobstructed view of a pressure sore or other injury site without even the slightest application of pressure to the injury site.

The first or second flaps may each be independently released from the upper. For example, releasing the first flap may allow the first side of the sole to be separated from the upper. Separating the first side of the sole from the upper may allow a practitioner to visually inspect or even treat an injury at or near the first side of the sole (e.g., on a medial side of the patient's foot). Releasing the first flap from the upper or separating the first side of the sole from the upper may not apply any pressure to the patient's foot and/or leg. After releasing the first flap, the second flap and second side of the sole may remain affixed to the upper.

Releasing the second flap may allow the second side of the sole to be separated from the upper. Separating the second side of the sole from the upper may allow a practitioner to visually inspect or even treat an injury at or near the second side of the sole (e.g., on a lateral side of the patient's foot). Releasing the second flap from the upper or separating the second side of the sole from the upper may not apply any pressure to the patient's foot and/or leg. After releasing the second flap, the first flap and first side of the sole may remain affixed to the upper.

Releasing the first flap from the upper may allow a first segment of the upper to rotate with respect to a second segment of the upper. The first segment of the upper may rotate to uncover the medial side of the patient's leg. Uncovering the medial side of the leg may allow a practitioner to visually examine an injury site at or near the medial side of the patient's leg.

Releasing the second flap from the upper may allow a third segment of the upper to rotate with respect to the second segment of the upper. The third segment of the upper may rotate to uncover the lateral side of the patient's leg. Uncovering the lateral side of the leg may allow a practitioner to visually examine an injury site at or near the lateral side of the patient's leg.

In some embodiments, the strap that affixes the first segment to the third segment may be placed over the second end of the first or second flap. In such embodiments, the strap must be released before a practitioner is able to release the second end of the first or second flap from the upper. In some embodiments, the strap that affixes the first segment to the third segment may be placed under the second end of the first or second flap. In such embodiments, the second end of the first or second flap may be released without releasing the strap.

The first flap may be spaced apart from the first hinge connecting the sole to the upper. The second flap may be spaced apart from the second hinge connecting the sole to the upper. The space between the first flap and the first hinge or the space between the second flap and the second hinge may allow for tubing of a deep vein thrombosis ("DVT") prevention system to be inserted into the boot.

The sole may include a first section and a second section. The sole may be configured to bend about a joint between the first section and the second section. The sole may bend about the joint and minimize any pressure applied to the plantar surface of the patient's foot/leg when the sole is in the closed position.

The upper may define a space between the first segment of the upper and the second segment of the upper. The space between the first and second segments may provide room for inserting tubing of a deep vein thrombosis ("DVT") prevention system. The upper may define a space between the third segment of the upper and the second segment of the upper. The space between the first and third segments may provide room for inserting tubing of deep vein thrombosis ("DVT") prevention system.

A therapeutic boot is provided. The boot may include an upper. The upper may refer to all parts of the boot above a sole of the boot. The upper may define a plantar surface. The plantar surface may be defined by first, second and third segments of the upper. The first segment of the upper may be configured to cover a first side of a patient's foot or leg. The first side may be a medial side of the patient's foot or leg. The first segment may be rotatable to expose or cover the medial side of the patient's foot and/or leg.

The second segment may be configured to cover a second side of a patient's foot and/or leg. The second side may be a dorsal side of the patient's foot and/or leg. The second segment of the upper may support the dorsal side of the patient's foot and/or leg. The third segment of the upper may be configured to cover a third side of a patient's foot and/or leg. The third side may be a lateral side of the patient's foot and/or leg. The third segment may be rotatable to expose or cover the lateral side of the patient's foot and/or leg.

The boot may include a sole. The sole may be affixed to the upper by a hinge. The hinge may link the sole to the second segment of the upper. The hinge may link a heel end of the sole to a heel end of the upper. The hinge may allow the sole to rotate between a closed position and an open position. In the closed position, the sole may cover the plantar surface defined by the upper. In the open position, the sole may expose the plantar surface. In the open position, the sole may not obstruct access to an interior of the boot. Exposing the plantar surface may provide access to the interior of the boot. The "interior" of the boot refers to the surfaces or sides of the boot that contact the patient's leg and/or foot when the patient is wearing the boot. When the sole is in the open position, a practitioner may visually inspect and treat a pressure sore or other injury on a foot/leg of a patient wearing the boot.

The upper may define a cut-out at the heel end of the upper. The cut-out may correspond to a location of what otherwise would have been a heel pocket of the boot. The second segment of the upper may define the cut-out. A heel portion of bedridden patient's foot may be particularly susceptible to developing a pressure sore. The second segment of the upper may elevate a patient's foot and/or leg. When the patient's foot is positioned in the boot, the cut-out is configured to suspend or offload the heel portion of the patient's foot, relieving any pressure from being applied to the injury site.

The second segment of the upper may be configured to be positioned underneath a patient's leg. The second segment may be configured to elevate the patient's foot. The first segment of the upper may be rotatable with respect to the second segment. The third segment of the upper may be rotatable with respect to the second segment.

The boot may include a strap. The strap may be configured to join the first segment to the third segment. The strap may be configured to hold the first segment in a position relative to the third segment. For example, the strap may hold the first segment parallel to the third segment. The strap may be configured to hold the first or third segment in a position relative to the second segment. For example, the strap may be configured to hold the third segment perpendicular to the second segment.

The first segment may be rotated (e.g., with respect to the second segment) to expose or cover a first side of the patient's foot and/or leg. In a first position, the first segment may be positioned to cover the patient's foot and/or leg. When the first segment is in the first position, the sole may be in the open or in the closed position. In the first position, the first segment may be positioned parallel the second segment. In the first position, the first segment may be positioned at an angle greater than 180 degrees with respect to the second segment.

Angular measurements relative to the second segment may be measured relative to an interior of the second segment. The "interior" may refer to a surface or side (e.g., of the second segment) that contacts the patient's leg and/or foot when the patient is wearing the boot.

In a second position, the first segment may be positioned at an angle between 0 and 90 degrees with respect to the second segment. When the first segment is in the second position, the sole may be in the open or the closed position. In the second position, the first segment may be positioned such that a side (e.g., medial side) of the patient's foot and/or leg is at least partially exposed. For example, rotating the first segment to a position 45 degrees with respect to the second segment may allow a practitioner to view and access parts of the patient's leg and/or foot at or near an intersection of the medial and ventral sides of the patient's leg and/or foot.

The first segment of the upper and the sole may each be independently rotated relative to the second segment of the upper. The second segment of the upper may be positioned to support or cover a dorsal side of a patient's foot and/or leg. The first segment of the upper may be rotated in a direction away from the patient's foot and/or leg without applying any pressure to the patient's foot and/or leg and thereby minimizing any irritation to a pressure sore injury. Thus, various segments of the boot may be rotated to expose the patient's foot and/or leg. Exposing the patient's foot and/or leg by rotating a segment may allow a practitioner to visually examine or access a pressure sore injury site without any risk of irritating the injury.

Methods of protecting a foot and/or leg of a patient are provided. The patient may be bedridden. The methods may include positioning a second segment of a boot upper underneath a dorsal side of the patient's leg and/or foot. Methods may include positioning a stabilizer underneath or next to the second segment of the upper. The stabilizer may prevent rotational movement of the boot when the patient's foot and/or leg is inserted into the boot. Methods may include positioning a first segment of the boot upper to protect a medial side of the patient's leg and/or foot. Positioning the first segment may include rotating the first segment relative to the second segment.

Methods may include positioning a third segment of the boot upper to protect a lateral side of the patient's leg and/or foot. Positioning the third segment may include rotating the third segment relative to the second segment. Methods may include positioning a sole segment of the boot to cover a plantar surface of the patient's foot. Positioning the sole segment may include rotating the sole segment relative to one or more segments of the upper.

Methods may include affixing the sole segment to the first segment of the upper. Methods may include affixing the sole segment to the third segment of the upper. The sole segment may be releasably affixed to the first and third segments. Methods may include releasing the sole segment from the first segment. Methods may include releasing the sole segment from the first segment without applying pressure to the plantar surface of the patient's foot.

Methods may include releasing the sole segment from the third segment. Methods may include releasing the sole segment from the third segment without applying pressure to the plantar surface of the patient's foot. Methods may include rotating the sole segment relative to one or more segments of the upper. Methods may include rotating the sole segment to expose the plantar surface of the patient's foot without applying pressure to the patient's foot.

Methods may include rotating one or more segments of the upper away from the patient's leg and/or foot without applying pressure to the patient's leg and/or foot. For example, methods may include rotating the first segment of the upper away from or closer to the medial side of the patient's leg and/or foot. Methods may include rotating the third segment of the upper away from or closer to the lateral side of the patient's leg and/or foot.

Methods may include releasing the sole segment from the first and third segments. Methods may include rotating a toe end of the sole segment away from the first and third segments. Methods may include inserting a device configured to prevent and relieve deep vein thrombosis into an opening between the sole segment and the boot upper.

Methods may include inserting a device configured to prevent and relieve deep vein thrombosis into an opening defined by the sole segment.

Methods of operation for a therapeutic boot are provided. The boot may include an upper and a sole segment. The upper may include a first segment, a second segment and a third segment. The methods may include positioning a first segment of the upper relative to a second segment of the upper. The first segment may be positioned perpendicular to the second segment. Positioning the first segment relative to the second segment may include rotating the first segment relative to the second segment. The first segment may be rotated about a joint linking the first segment to the second segment.

The methods may include positioning a third segment of the upper relative to the second segment of the upper. The third segment may be positioned perpendicular to the second segment. Positioning the third segment relative to the second segment may include rotating the third segment relative to the second segment. The third segment may be rotated about a joint linking the third segment to the second segment.

The methods may include releasably affixing the first segment to the third segment. For example, the first segment may be releasably affixed to the third segment by a strap. A first end of the strap may be affixed to either the first segment or the third segment. A second end of the strap may be releasably affixed to either the first segment or the third segment. A middle portion of the strap may pass over the second segment. A middle portion of the strap may pass over a space between the first and third segments. A patient's foot and/or leg may be positioned above the second segment in the space between the first and third segments.

The methods may include positioning a sole segment to cover a plantar surface defined by the therapeutic boot. The plantar surface may be defined by the first, second and third segments. The plantar surface may be defined when the second segment is positioned perpendicular to the first and third segments. The strap may hold the first and third segments in a position perpendicular to the second segment.

The methods may include positioning the sole segment to cover the plantar surface by rotating the sole segment about hinge that links the sole segment to the second segment of the upper. The methods may include positioning the sole segment parallel to, or at an angle greater than 90 degrees relative to, the second segment. Angular measurements of the sole segment with respect to the second segment may be measured relative to an interior of the sole and second segment.

Repositioning of the sole segment relative to the second segment may not apply pressure to patient's foot or leg positioned in the therapeutic boot. Repositioning of the sole segment relative to the second segment may uncover the plantar surface defined by the upper. Uncovering the plantar surface may allow a practitioner access to an interior of the therapeutic boot. Uncovering the plantar surface may allow a practitioner access to a patient's foot and/or leg when the foot and/or leg is positioned in the therapeutic boot.

Apparatus and methods in accordance with this disclosure will now be described in connection with the figures, which form a part hereof. The figures show illustrative features of apparatus and method steps in accordance with the principles of this disclosure. It is to be understood that other embodiments may be utilized, and that structural, functional and procedural modifications may be made without departing from the scope and spirit of the present disclosure.

The steps of methods may be performed in an order other than the order shown and/or described herein. Method embodiments may omit steps shown and/or described in connection with illustrative methods. Method embodiments may include steps that are neither shown nor described in connection with illustrative methods. Illustrative method steps may be combined. For example, an illustrative method may include steps shown in connection with any other illustrative method.

Apparatus may omit features shown and/or described in connection with illustrative apparatus. Apparatus embodiments may include features that are neither shown nor described in connection with illustrative apparatus. Features of illustrative apparatus may be combined. For example, an illustrative apparatus embodiment may include features shown or described in connection with another illustrative apparatus/method embodiment.

FIG. 1 shows illustrative therapeutic boot 100. Boot includes sole segment 101. Boot includes first flap 113. First end 115 of first flap 113 is rotatably affixed to sole segment 101. Second end 117 of first flap 113 is releasably affixed to first upper segment 103. FIG. 1 shows first upper segment 103 positioned parallel to third upper segment 111. FIG. 1 shows first upper segment 103 and third upper segment 111 positioned perpendicular to sole segment 101. FIG. 1 shows first upper segment 103 and third upper segment 111 positioned perpendicular to second upper segment 105.

FIG. 1 shows that first upper segment 103 is releasably affixed to third upper segment 111 by straps 107 and 109. First ends of straps 107 and 109 are rotatably affixed to third upper segment 111. Second ends of straps 107 and 109 are releasable affixed to first upper segment 103. FIG. 1 also shows that a middle portion of straps 107 and 109 passes over a space between first upper segment 103 and third upper segment 111.

FIG. 1 also shows that straps 107 and 109 hold first upper segment 103 and third upper segment 111 in a position relative to second upper segment 105. FIG. 1 shows that straps 107 and 109 hold first upper segment 103 and third upper segment 111 in a position perpendicular to second upper segment 105.

Figure 2:
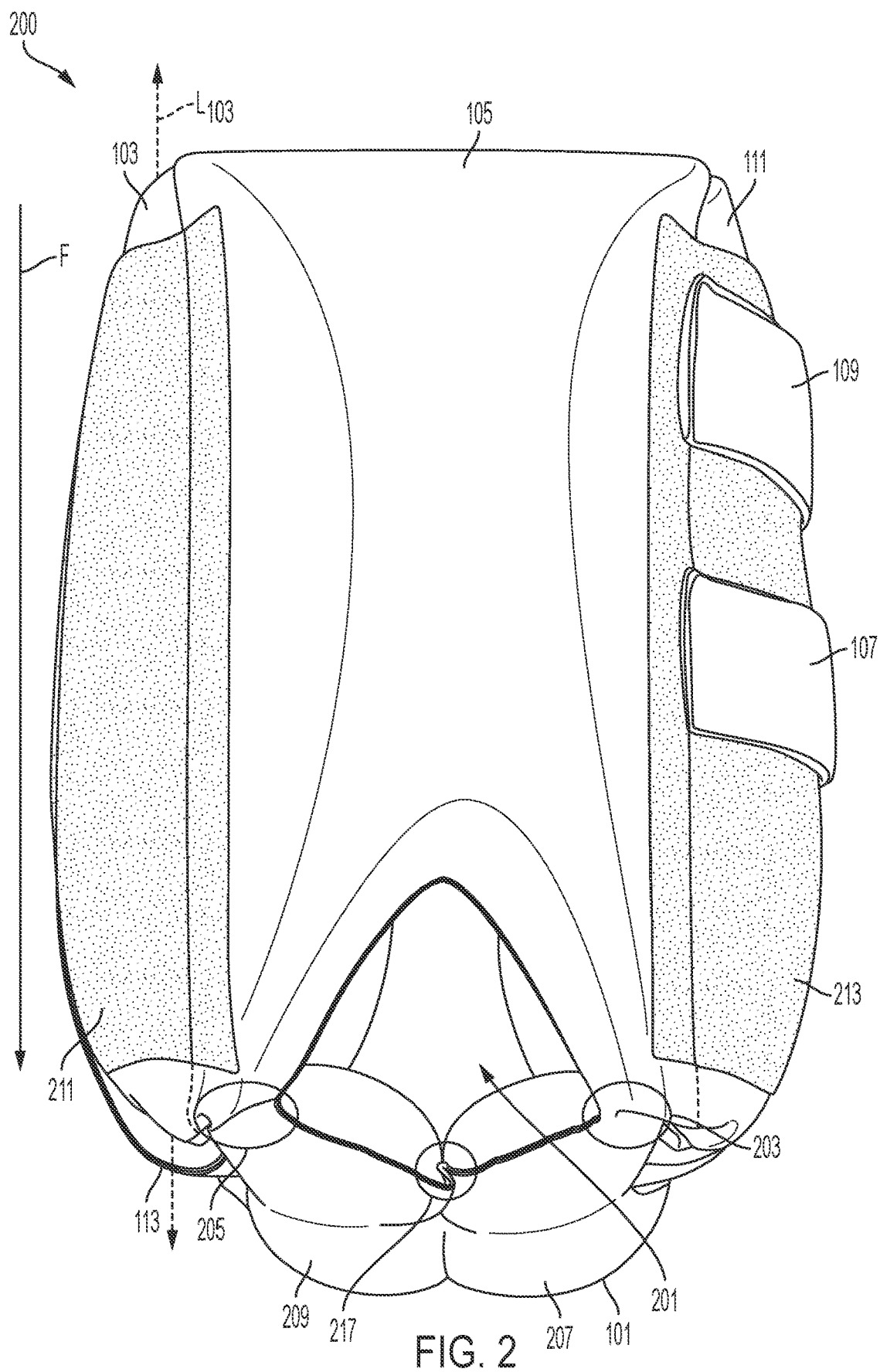
FIG. 2 shows another view of the illustrative boot shown in FIG. 1 in accordance with principles of the disclosure.

FIG. 2 shows illustrative view 200 of therapeutic boot 100 (shown in FIG. 1). View 200 shows second upper segment 105. Second upper segment 105 may be positioned underneath a leg and/or foot of a bedridden patient. Second upper segment 105 may space the patient's foot and/or leg apart from a bed supporting the patient. Second upper segment 105 defines cut-out 201. Cut-out 201 is configured to suspend a heel the patient's foot above the bed supporting the patient.

View 200 shows that sole segment 101 may include first sole section 209 and second sole section 207. First sole section 209 and second sole section 207 are configured to bend about joint 217. View 200 shows that in conjunction with cut-out 201, the bending about joint 217 allows sole segment 101 to avoid or only have minimal contact with a patient's foot. Minimizing contact with the patient's foot may promote healing of pressure sores on the foot. Minimizing contact with the patient's foot may reduce pain associated with contact with pressure sores on the foot.

View 200 shows that boot 100 includes loops 211 on first upper segment 103. Hooks (not shown) on first flap 113 (shown in FIG. 1) may be configured to mate with loops 211 and fasten first flap 113 to first upper segment 103. View 200 shows that boot 100 includes loops 213 on third upper segment 111. Hooks (not shown) on a second flap (not shown) may be configured to mate with loops 213 to fasten a second flap to third upper segment 111. A flap may include the loops and the segment may include the hoops.

View 200 also shows that sole segment 101 is rotatably connected to second upper segment 105 by hinges 203 and 205. Hinges 203 and 205 allow sole segment 101 to rotate relative to second upper segment 105. First flap 113 when fastened to first upper segment 103 and the second flap (not shown) when fastened to third upper segment 111 may hold sole segment 101 in a position relative to second upper segment 105. For example, the flaps may hold sole segment 101 in a closed position.

Releasing first flap 113 from first upper segment 103 may allow first sole segment 209 to be moved apart from first upper segment 103 and second upper segment 105. Moving first sole segment 209 may allow a practitioner to obtain visual access to an injury site on a patient's foot positioned inside boot 100.

Releasing a second flap (not shown) affixing third upper segment 111 to second sole segment 207 may allow a practitioner to obtain visual access to an injury site on a patient's foot positioned inside boot 100. After releasing the second flap, second sole segment 207 may be movable apart from third upper segment 111 and second upper segment 105. Moving second sole segment 207 may allow a practitioner to obtain visual access to an injury site on a patient's foot positioned inside boot 100.

Releasing both first flap 113 and a second flap (not shown) may allow sole segment 101 to be moved apart from first upper segment 103, second upper segment 105 and third upper segment 111. Releasing the first flap 113 and the second flap may not apply pressure to a patient's foot positioned inside boot 100. Force vector F shows that an illustrative direction of force applied to release flap 113 may be aligned along longitudinal axis $L_{103}$ of first upper segment 103. A force vector needed to separate flap 113 from first upper segment 103 may include other de minimis components that are not aligned with force vector F. However, any such de minimis force components may not be significant enough to apply pressure to a patient's foot and/or leg positioned inside boot 100.

Sole segment 101 may be moved such that a practitioner has unobstructed access to a foot of a patient wearing boot 100. Sole segment 101 may be moved relative to first upper segment 103, second upper segment 105 and third upper segment 111 such that a plantar surface defined by the upper segments 103, 111 and 105 is completely unobstructed by sole segment 101.

Figure 3:
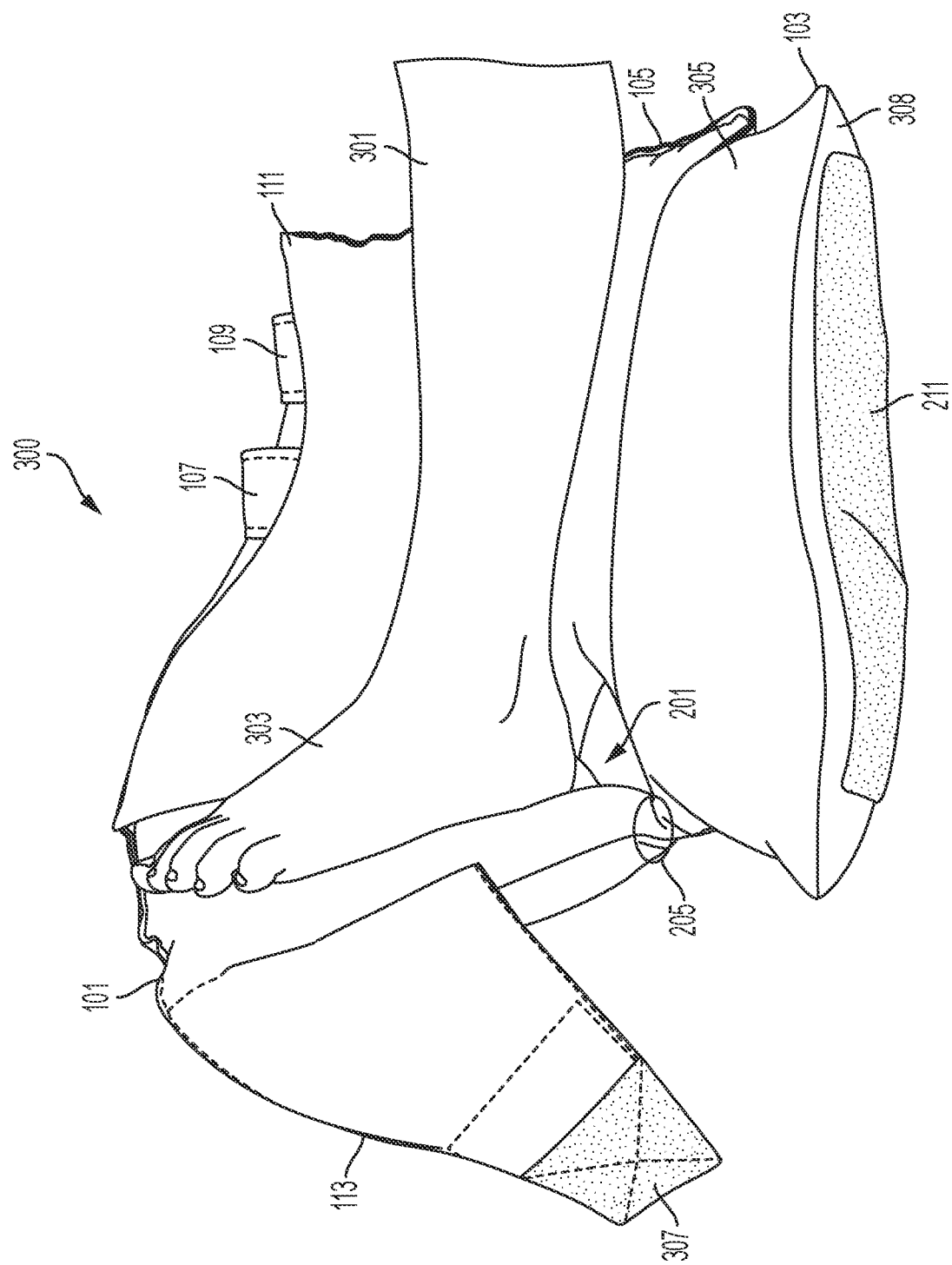
FIG. 3 shows illustrative features of the boot shown in FIG. 1 in connection with a therapeutic scenario and in accordance with principles of the disclosure.

FIG. 3 shows illustrative features of boot 100 in connection with illustrative therapeutic scenario 300. Scenario 300 shows leg 301 and foot 303 of a patient positioned in boot 100. Scenario 300 shows that first flap 113 has been released from first upper segment 103. Scenario 300 shows that straps 107 and 109 have been released from first upper segment 103. Releasing first flap 113 requires separating loops 211 from hooks 307. Releasing straps 107 and 109 requires separating hooks (not shown) on second ends of straps 107 and 109 from loops 211.

Releasing second end 117 (shown in FIG. 1) of first flap 113 and second ends of straps 107 and 109 allows first upper segment 103 to be rotated relative to second upper segment 105. Scenario 300 shows that first upper segment 103 has been rotated relative to second upper segment 105 to expose leg 301 and foot 303. Exposing leg 301 and foot 303 allows a practitioner to examine and treat any pressure sores or other injuries on leg 301 or foot 303 without removing leg 301 or foot 303 from boot 100. The releasing of first flap 113 and straps 107 and 109 may not apply pressure to leg 301 or foot 303. First upper segment 103 may be rotated relative to second upper segment 105 without applying pressure to leg 301 or foot 303.

Scenario 300 shows that first end 115 (shown in FIG. 1) of flap 113 remains affixed to sole segment 101. Scenario 300 shows that first ends of straps 107 and 109 remain affixed to third upper segment 111. FIG. 3 also shows that first upper segment 103 includes interior surface 305 and exterior surface 308. Interior surface 305 may include an antimicrobial fabric that promotes air circulation and wicks away moisture. Exterior surface 308 may be nylon which may be easily wiped clean.

Scenario 300 shows that a heel portion of foot 303 is suspended over cut-out 201. Suspending or "offloading" the heel portion of foot 303 over cut-out 201 may promote healing of a pressure sore on or near the heel portion.

Figure 4:
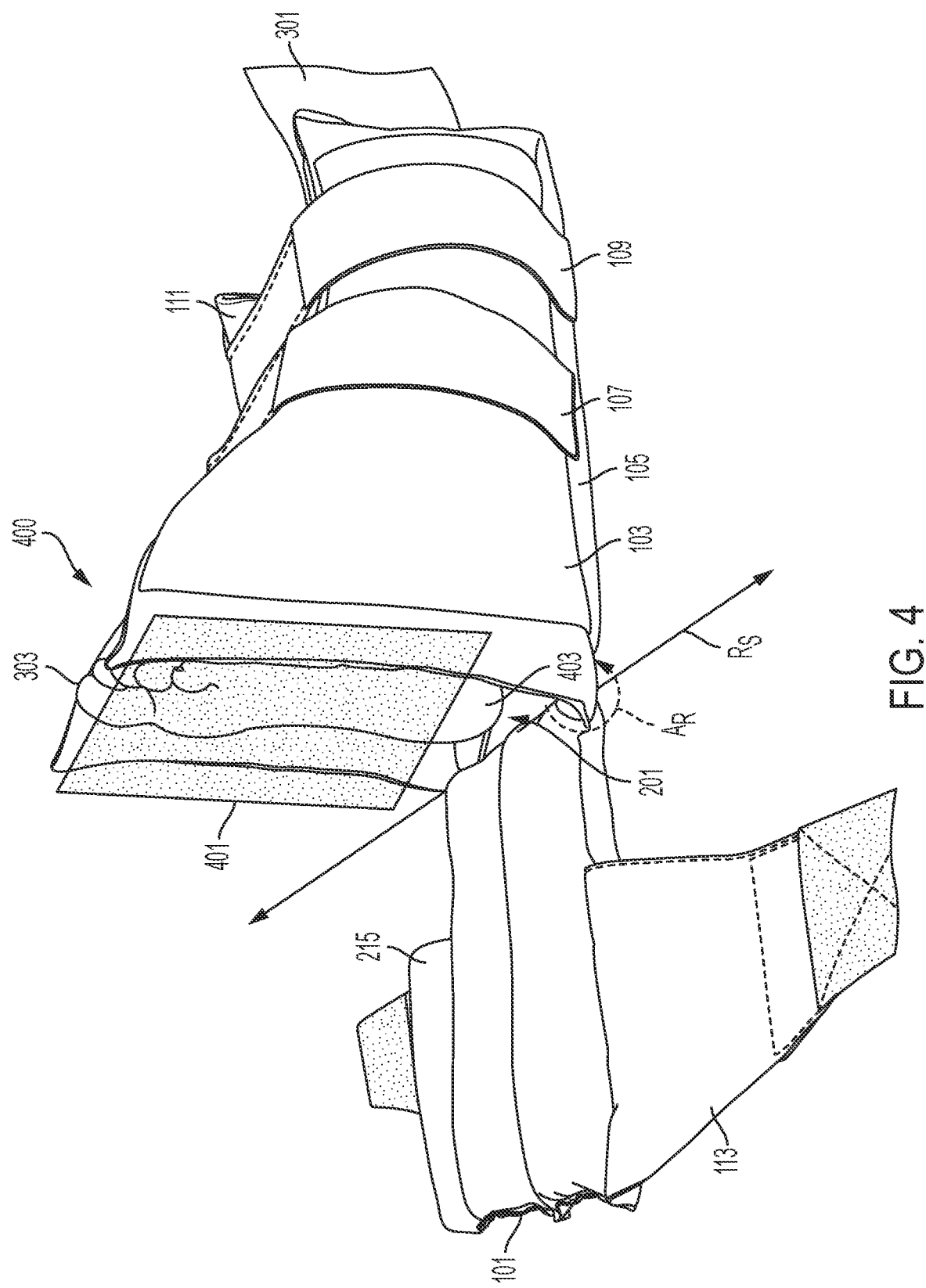
FIG. 4 shows illustrative features of the boot shown in FIG. 1 in connection with a therapeutic scenario and in accordance with principles of the disclosure.

FIG. 4 shows illustrative features of boot 100 in connection with illustrative therapeutic scenario 400. Scenario 400 shows that second end 117 (shown in FIG. 1) of flap 113 has been released from first upper segment 103.

Scenario 400 also shows that a second end of flap 215 has been released from third upper segment 111. After releasing second ends of flaps 113 and 215, sole segment 101 has been rotated about hinges 203 and 205 (shown in FIG. 2) to expose plantar surface 401. Plantar surface 401 is defined by first upper segment 103 and third upper segment 111 being positioned parallel to each other and perpendicular to second upper segment 105. FIG. 4 shows that plantar surface 401 may be parallel to a plantar surface of foot 303 positioned inside boot 100.

Scenario 400 shows that sole segment 101 may be rotated about axis $R_S$. Sole segment 101 may be rotated following rotational path $A_R$ to completely expose plantar surface 401 and provide unobstructed access to a plantar surface of foot 303. Scenario 400 also shows that sole segment 101 may be rotated without applying any pressure to foot 303 or a pressure sore injury on foot 303. Scenario 400 also shows that foot 303 is positioned in boot 100 such that heel portion 403 of foot 303 is suspended above cut-out 201.

Figure 5:
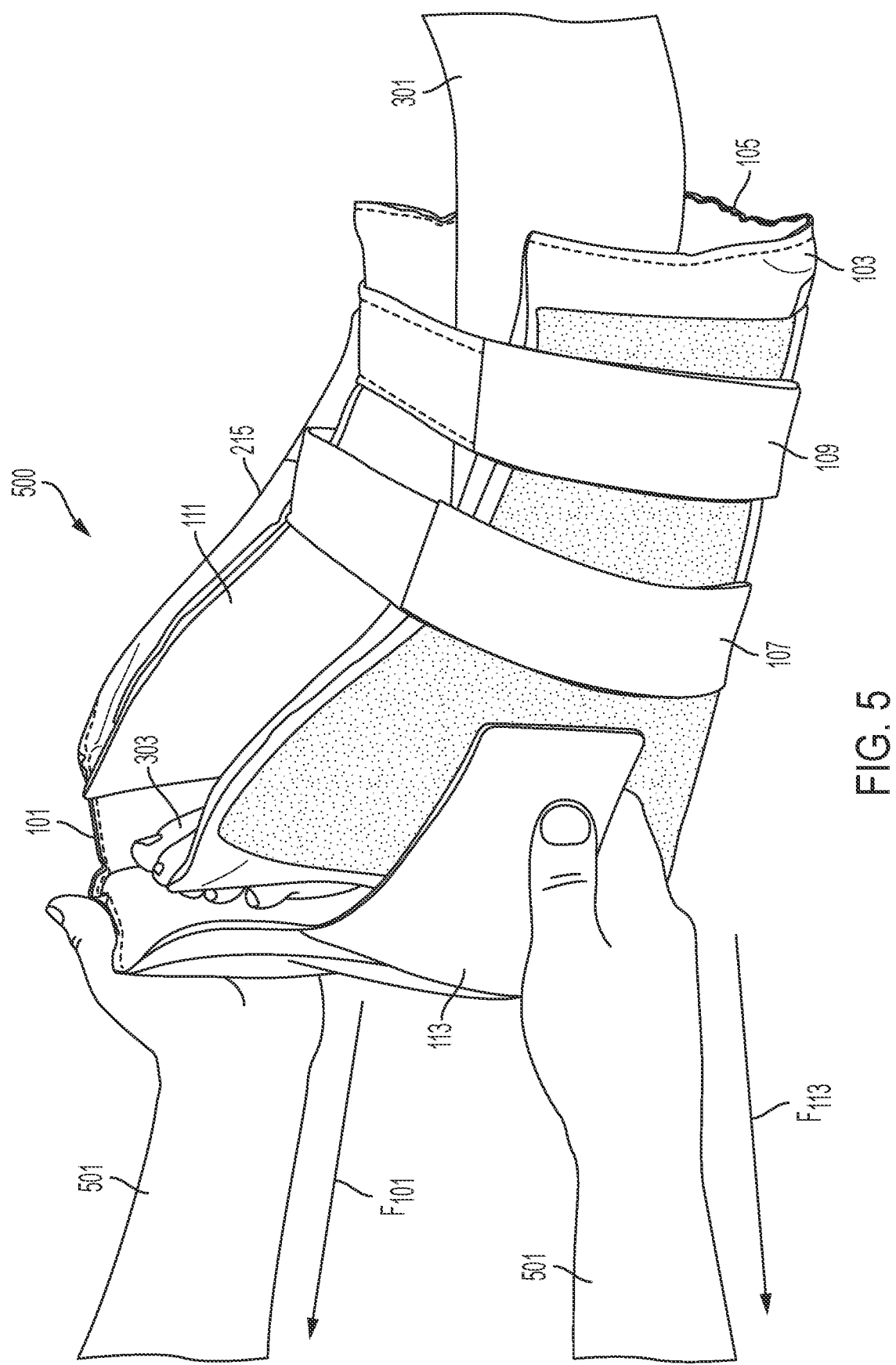
FIG. 5 shows illustrative features of the boot shown in FIG. 1 in connection with a therapeutic scenario and in accordance with principles of the disclosure.

FIG. 5 shows illustrative features of boot 100 in connection with illustrative therapeutic scenario 500. In scenario 500, practitioner 501 is in the processes of releasing second end 117 (shown in FIG. 1) of flap 113 from first upper segment 103 and rotating sole segment 101 to gain access patient's foot 303. Practitioner 501 may wish to rotate sole segment 101 to examine or treat a pressure sore on foot 303.

Pressure sores are extremely sensitive to even the slightest touch or contact. Scenario 500 shows that boot 100 has been designed such that practitioner 501 does not apply any pressure to foot 303 when releasing flap 113 or rotating sole segment 101 into an open position. Scenario 500 shows that to release flap 113, practitioner 501 applies force $F_{113}$. Force $F_{113}$ is a vector directed away from foot 303. Thus, when force $F_{113}$ is applied to release flap 113, force $F_{113}$ will not cause a component or segment of boot 100 to contact foot 303 or a pressure sore injury site on foot 303.

Scenario 500 also shows that boot 100 has been designed such that practitioner 501 does not apply any pressure to foot 303 when rotating sole segment 101. Scenario 500 shows that to move sole segment from a closed positioned (as shown in FIG. 5) into an open position (as shown in FIG. 4), practitioner 501 applies force $F_{101}$. Force $F_{101}$ is a vector that is directed away from foot 303. Thus, when force $F_{101}$ is applied to move sole segment 101 from the closed position into the open position, force $F_{101}$ will not cause a component or segment of boot 100 to contact foot 303 or a pressure sore injury site on foot 303.

Scenario 500 also shows that flap 113 may be positioned over first ends of straps 107 and 109. Scenario 500 shows that flap 113 may be released even when first ends of straps 107 and 109 remain affixed to first upper segment 103.

Figure 6:
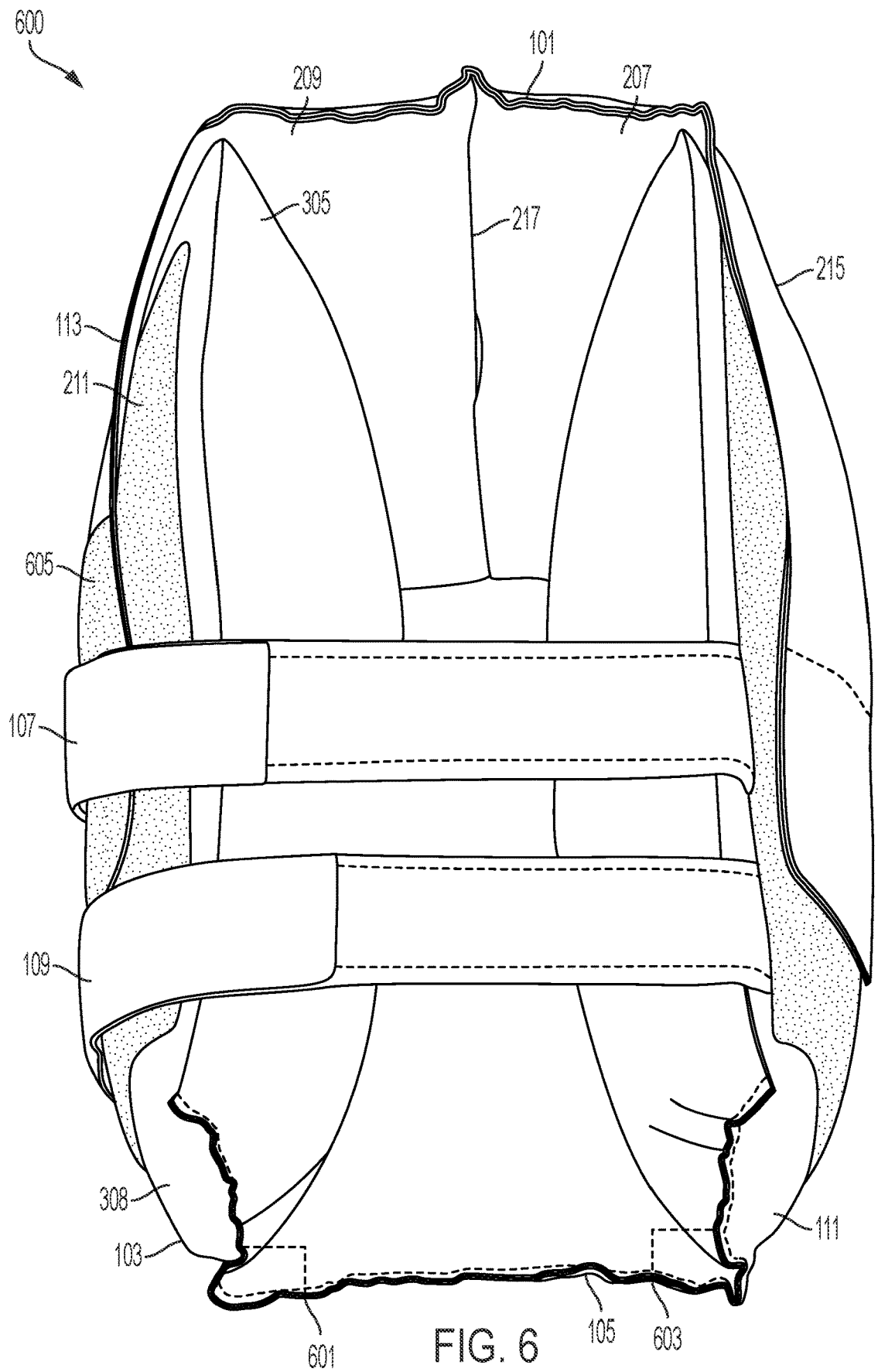
FIG. 6 shows another view of the illustrative boot shown in FIG. 1, in accordance with principles of the disclosure.

FIG. 6 shows illustrative top-down view 600 of boot 100. View 600 shows that straps 107 and 109 are holding first upper segment 103 at a 90-degree angle (reference 601) relative to second upper segment 105. Straps 107 and 109 are holding third upper segment 111 at 90-degree angle (reference 603) relative to second upper segment 105. Straps 107 and 109 are holding first upper segment 103 parallel to third upper segment 111.

View 600 shows that a space between first upper segment 103 and third upper segment 111 may be left open. Leaving the space between first upper segment 103 and third upper segment 111 open may enhance the circulation of air flow around leg 301 and foot 303, when positioned on second upper segment 105 and in the space between first upper segment 103 and third upper segment 111.

View 600 shows that flap 113 may be positioned underneath straps 107 and 109. Flap 113 may include hooks 307 (shown in FIG. 3) that are configured to mate with loops 211 on exterior surface 308 of first upper segment 103. Flap 113 may also include loops 605. Hooks (not shown) may be positioned on an underside of straps 107 and 109. The hooks on straps 107 and 109 may mate with loops 605 and/or 211 to secure straps 107 and 109.

Figure 7:
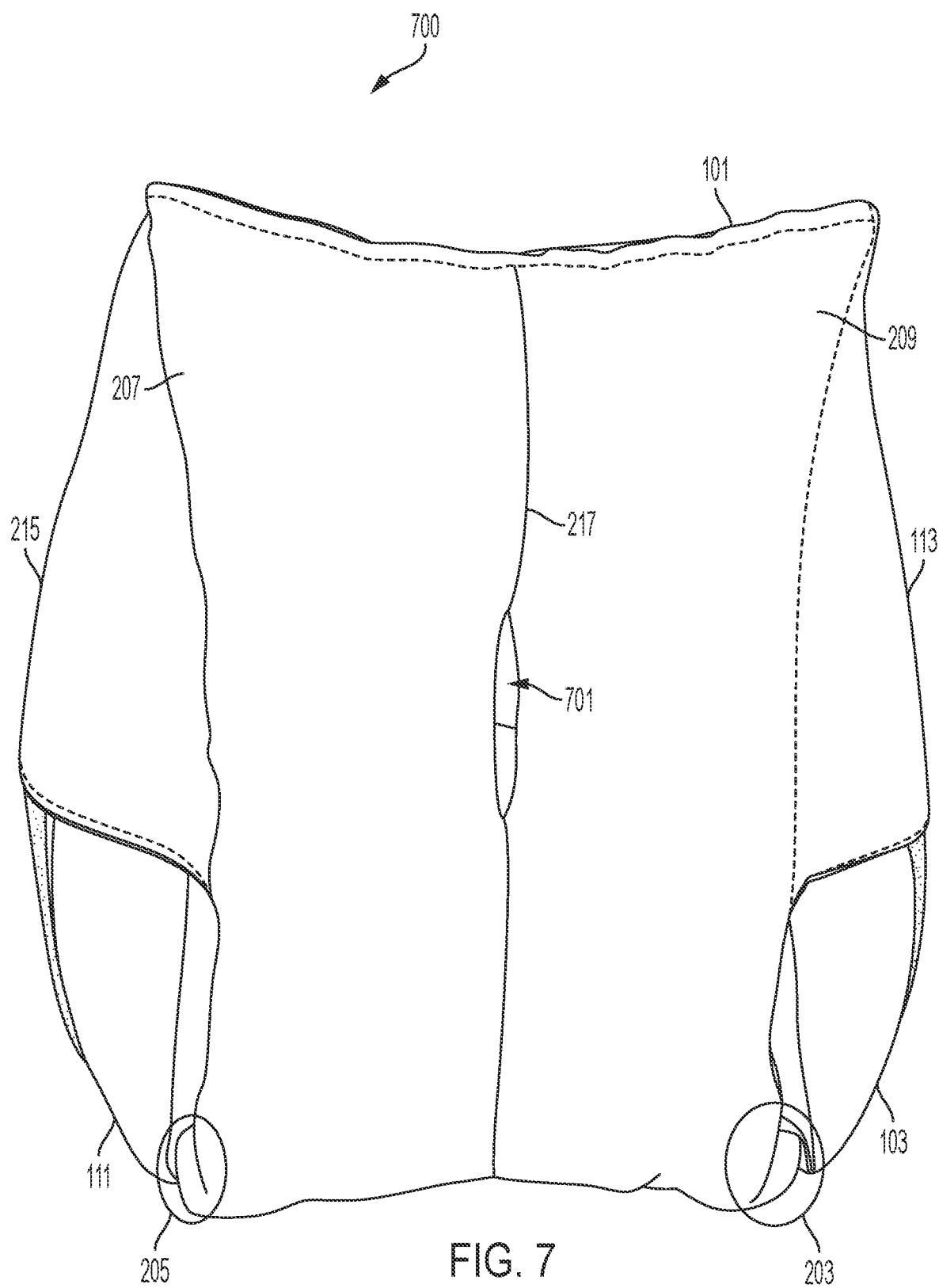
FIG. 7 shows another view of the illustrative boot shown in FIG. 1 in accordance with principles of the disclosure.

FIG. 7 shows illustrative view 700 of boot 100. View 700 shows sole segment 101 in a closed position. View 700 shows that sole segment 101 include cut-out 701. Cut-out 701 provides space for insertion of tubing of a deep vein thrombosis ("DVT") prevention system.

Figure 8:
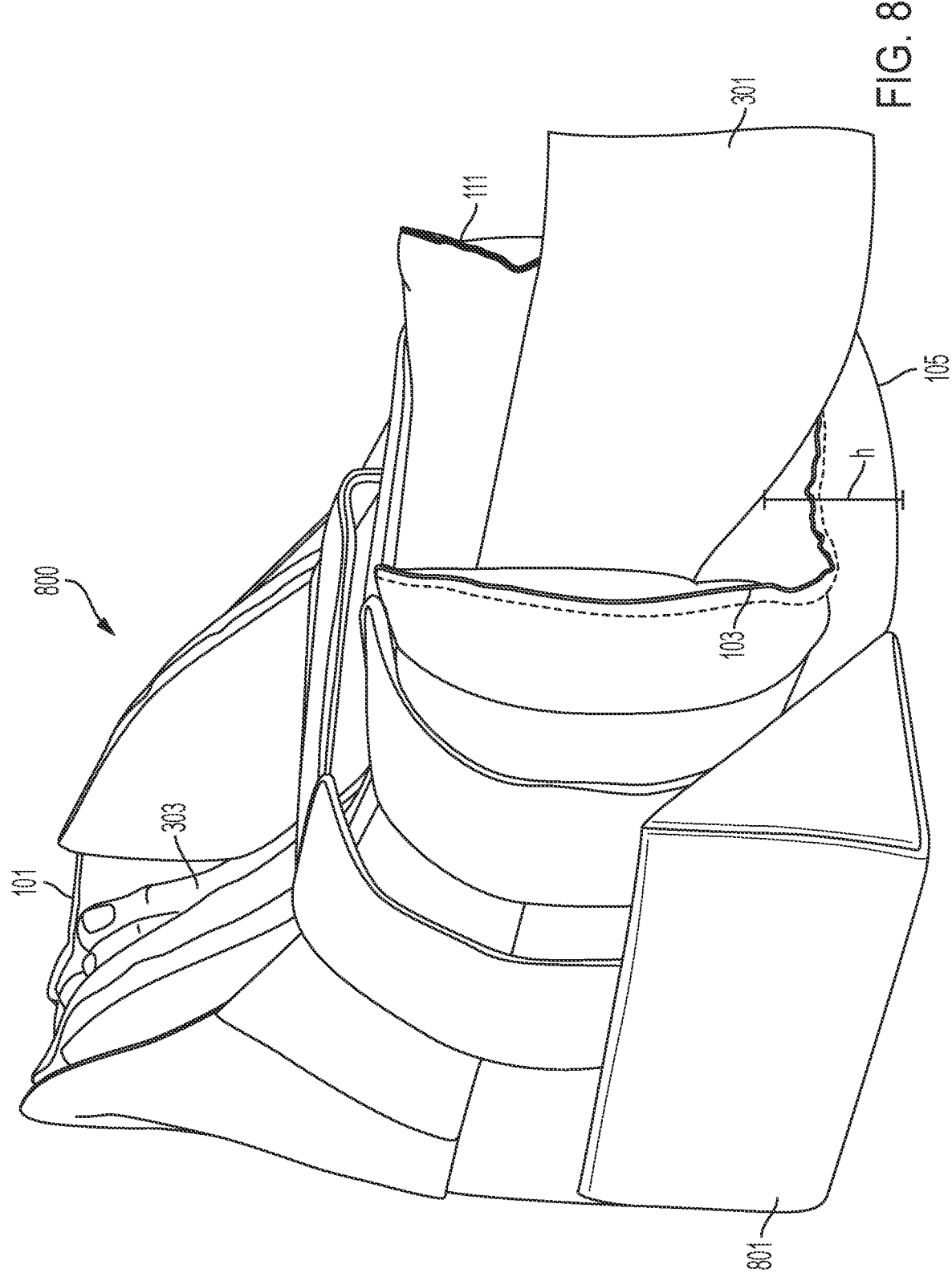
FIG. 8 shows an illustrative therapeutic scenario using the boot shown in FIG. 1 and in accordance with principles of the disclosure.

FIG. 8 shows illustrative therapeutic scenario 800. Scenario 800 shows patient's leg 301 and foot 303 positioned in boot 100. Boot 100 is providing suspension or "offloading" of a heel of foot 303. Scenario 800 shows that stabilizer 801 is positioned to maintain an orientation of boot 100. Stabilizer 801 is wedged between first upper segment 103 and second upper segment 105. Another stabilizer (not shown) may be wedged between third upper segment 111 and second upper segment 105.

Stabilizer 801 prevents boot 100 from being rotated in a first direction. A second stabilizer wedged between third upper segment 111 and second upper segment 105 prevents boot 100 from rotating in a second direction. Rotation of boot 100 may cause irritation to a pressure sore on foot 303. Scenario 800 also shows that second upper segment 105 elevates leg 301 by height h above a bed (not shown) supporting the patient.

Thus, methods and apparatus for a SIDES-DOWN, OPEN DOOR PRESSURE RELIEF BOOT are provided. Persons skilled in the art will appreciate that the present disclosure can be practiced by other than the described embodiments, which are presented for purposes of illustration rather than of limitation, and that the present disclosure is limited only by the claims that follow.

What is claimed is:

1. A therapeutic boot configured to suspend a heel of a bedridden human patient's foot, the therapeutic boot comprising:
   an upper comprising a segment configured to be positioned under a dorsal side of a leg of the human patient, the upper configured to:
   elevate the heel; and
   define a plantar surface that is configured to extend from a heel-end of the human patient's foot to a toe-end of the human patient's foot; and a sole affixed to the segment by a hinge that allows the sole to rotate about a heel end of the segment between an open position and a closed position;

wherein:
in the open position, the sole is positioned to expose the plantar surface; and
in the closed position, the sole is positioned to cover the plantar surface.

2. The therapeutic boot of claim 1 wherein the hinge is a first hinge and the sole is rotatably affixed to the segment by the first hinge and a second hinge.

3. The therapeutic boot of claim 1, wherein the segment is a first segment, the boot further comprising:
a first flap that is configured to releasably affix a first side of the sole to a second segment of the upper; and
a second flap that is configured to releasably affix a second side of the sole to a third segment of the upper.

4. The therapeutic boot of claim 3 wherein:
the first flap is separable from the second segment without applying pressure to the human patient's foot; and
the second flap is separable from the third segment without applying pressure to the human patient's foot.

5. The therapeutic boot of claim 1 wherein the sole is separable from the upper without applying pressure to the human patient's foot.

6. The therapeutic boot of claim 1 wherein the sole is rotatable from a first position at 90-degrees with respect to a longitudinal axis of the segment to a second position that is at 180-degrees or greater with respect to the longitudinal axis of the segment.

7. The therapeutic boot of claim 1 wherein:
the segment is a first segment of the upper, and wherein a second segment of the upper is rotatable with respect to the first segment of the upper; and
a third segment of the upper is rotatable with respect to the first segment of the upper.

8. The therapeutic boot of claim 7 wherein:
a first edge of the sole is separable from the second segment of the upper; and
a second edge of the sole is separable from the third segment of the upper.

9. The therapeutic boot of claim 1 wherein the segment is a first segment, and wherein the upper comprises:
a second segment configured to protect a medial side of the human patient's leg;
the first segment is configured to protect the dorsal side of the human patient's leg; and
a third segment configured to protect a lateral side of the human patient's leg; wherein the second segment is rotatable with respect to the first segment and the third segment is rotatable with respect to the first segment.

10. The therapeutic boot of claim 1, wherein the segment defines a cut-out that is configured to alleviate pressure on a dorsal side of a heel of the human patient's foot when the segment is positioned under the dorsal side of the leg.

11. A therapeutic boot comprising:
a first upper segment configured to cover at least a portion of a medial side of a leg of a bedridden human patient;
a second upper segment configured to cover at least a portion of a dorsal side of the leg;
a third upper segment configured to cover at least a portion of a lateral side of the leg; and
wherein the first, second and third upper segments are configured to define a plantar surface that extends from a heel-end of a foot of the human patient to a toe-end of the foot; and
a sole segment affixed to the second upper segment by a hinge that allows the sole segment to rotate about a heel end of the second upper segment between a closed position in which the sole segment covers the plantar surface and an open position in which the sole segment exposes the plantar surface.

12. The therapeutic boot of claim 11, wherein the hinge links a heel end of the sole segment to the heel end of the second upper segment.

13. The therapeutic boot of claim 11 wherein the second upper segment defines a cut-out that corresponds to a heel pocket.

14. The therapeutic boot of claim 11, wherein the first upper segment is rotatable with respect to the second upper segment and the third upper segment is rotatable with respect to the second upper segment.

15. The therapeutic boot of claim 14, wherein, the sole:
in the closed position is positionable perpendicular to a longitudinal axis of the second upper segment; and
in the open position is positionable at an angle 180 degrees or greater relative to the longitudinal axis of the second upper segment.

16. A method of protecting a foot and a leg of a bedridden human patient, the method comprising:
positioning a second segment of a boot upper underneath a dorsal side of the leg;
rotating and positioning a first segment of the boot upper to protect a medial side of the leg;
rotating and positioning a third segment of the boot upper to protect a lateral side of the leg; and
rotating a sole segment about a heel-end of the second segment to cover a plantar surface;
wherein the plantar surface is defined by the positioning of the first, second and third segments of the boot upper to protect the leg; and
wherein the plantar surface extends from a heel-end of the foot to a toe-end of the foot.

17. The method of claim 16 further comprising affixing the sole segment to the first segment and to the third segment.

18. The method of claim 17 further comprising:
releasing the sole segment from the first segment without applying pressure to the plantar surface of the foot; and
rotating the first segment away from the medial side of the leg.

19. The method of claim 17 further comprising:
releasing the sole segment from the third segment without applying pressure to the foot; and
rotating the third segment away from the lateral side of the leg.

20. The method of claim 16 further comprising rotating the sole segment away from the plantar surface to a position at an angle 180-degrees or greater with respect to the second segment.

* * * * *